United States Patent [19]

Maines

[11] Patent Number: 5,453,358
[45] Date of Patent: Sep. 26, 1995

[54] METHOD OF MEASURING CHOLESTEROL DIAGNOSING VASCULAR DISEASE

[76] Inventor: Robert Q. Maines, 123 Patterson St., Hillsdale, N.J. 07642

[21] Appl. No.: 941,669

[22] Filed: Sep. 8, 1992

Related U.S. Application Data

[63] Continuation of Ser. No. 297,080, Jan. 13, 1989, abandoned.

[51] Int. Cl.$^6$ .................................................. C12Q 1/60
[52] U.S. Cl. ................................. 435/11; 435/4; 435/15; 435/18; 435/19; 435/20; 435/25; 436/501; 436/13; 436/20; 436/166; 436/175; 436/805; 436/815
[58] Field of Search .................................. 435/4, 15, 18, 435/19, 20, 25, 11; 436/501, 13, 20, 166, 175, 805, 815; 426/73, 602, 648

[56] References Cited

U.S. PATENT DOCUMENTS

| | | | |
|---|---|---|---|
| 3,884,764 | 5/1975 | Goodhue et al. | 195/103.5 R |
| 4,184,921 | 1/1980 | Roeschlau et al. | 435/11 |
| 4,186,251 | 1/1980 | Tarbutton | 435/11 |
| 4,215,993 | 8/1980 | Sanders | 23/230 B |
| 4,414,326 | 11/1983 | Goldberg | 435/11 |
| 4,789,664 | 12/1988 | Seligson et al. | 514/23 |
| 4,851,335 | 7/1989 | Kerscher et al. | 435/11 |
| 4,892,815 | 1/1990 | Kerscher et al. | 435/7 |

FOREIGN PATENT DOCUMENTS

| | | |
|---|---|---|
| 0271963 | 6/1988 | European Pat. Off. . |
| 2097255 | 11/1982 | United Kingdom . |

OTHER PUBLICATIONS

Moshides (1988) Clin. Chem., vol. 34, No. 9, pp. 1799–1804.

J. S. Moshides, "High Density Lipoprotein Free Cholesterol and Other Lipids in Coronary Heart Disease," Arteriosclerosis, vol. 7, No. 3, May/Jun. 1987, pp. 262–266.

F. Grillo, et al., "Improved Method for Determination of High–Density–Lipoprotein Cholesterol II. Encymic Determination of Cholesterol in High–Density Lipoprotein Fractions with a Sensitive Reagent," Clinical Chemistry, vol. 27, No. 3, Mar. 1981, pp. 375–379.

Derwent Publications Ltd., London, GB, An 86–186014 and JP-A-61118323 (Pala Kasei Kogyo KK), World Patents Index Latest, week 8629.

Derwent Publications Ltd., London, GB, An 89–192700 and WO-A-8905354 (Adera-Manche Assoc.), World Patents Index Latest, week 8926.

Derwent Publications Ltd., London, GB, An 77–04726Y and JP-A-51139634 (Tamiya K), World Patents Index, week 7703.

Patent Abstracts of Japan, vol. 121, No. 48 (C-493), May 7, 1988, JP-A-62263119 (Nippon Oil & Fat Co., Ltd.) Nov. 16, 1987.

Lehninger (1970) *Biochemistry* (Worth Publishers, Inc., New York, New York) pp. 190, 195, 217, and 521.

*Primary Examiner*—Margaret Parr
*Assistant Examiner*—Ardin H. Marschel
*Attorney, Agent, or Firm*—Hopgood, Calimafde, Kalil & Judlowe

[57] ABSTRACT

A method is provided for measuring the net HDL cholesterol in the blood. The LDL and VLDL moieties are precipitated out and the remaining cholesterol content of the supernatant is measured. The free cholesterol content of the supernatant is separately measured and substracted from the total to obtain net HDL cholesterol. This value serves as a useful indicator for diagnosing vascular disease. A diet supplement and method for raising serum HDL is provided.

3 Claims, No Drawings

METHOD OF MEASURING CHOLESTEROL DIAGNOSING VASCULAR DISEASE

This is a continuation of U.S. application Ser. No. 07/297,080 filed on Jan. 13, 1989, now abandoned.

BACKGROUND OF THE INVENTION

This invention relates to the measurement of various forms of cholesterol in the bloodstream of mammals, the diagnosis of vascular disease or atherosclerosis from such measurements, and a method of raising HDL cholesterol levels.

Serum total cholesterol consists of both esterified and unesterified cholesterol fractions bound in varying amounts to several lipoprotein carriers. Approximately 71–75% of the total cholesterol is esterified, i.e. bonded to fatty esters. Unesterified (free) cholesterol, an insoluble, abrasive waxy alcohol, makes up about 25–29% of the total. Chylomicrons, very large particles containing essential lubricating lipids, are produced in the duodenum and jejunum and play a role in the absorption of the essential fatty acids and phospholipids needed to form lipoprotein particles. Chylomicrons transport triglycerides (TG) from the intestines to the liver.

Low-density lipoprotein (LDL), the major cholesterol carrier, is a spherical particle consisting of about 50% cholesterol, 20% protein and 25% phospholipids. Very low-density lipoprotein (VLDL), a liver-generated precursor of LDL, is a large particle composed of 15–25% cholesterol and, mainly, triglycerides. LDL and VLDL have been implicated in atherosclerosis. VLDL particles typically have a life span of 4–5 hours, while LDL particles last 2–3 days.

High-density lipoprotein (HDL), a small particle obtaining about 20% cholesterol, 50% protein, and 25% phospholipids, appears to play a major role in the exchange of free cholesterol between cells, the liver, and other lipoprotein moieties. Free cholesterol is needed in red blood cells, lipoprotein moieties, and most cell structures. High levels of HDL are believed to lower the incidence of cardiovascular disease.

Blood tests to determine total serum cholesterol are commonly used to assess the risk of heart disease. However, since not all types of cholesterol indicate high risk, total serum cholesterol is not a very reliable indicator below 300 mg/dl. Consequently, attempts have been made to separately measure the HDL fraction. Typically, the LDL and VLDL fractions are precipitated out of solution and the cholesterol entities remaining in the supernatant are measured. These entities are assumed to be HDL. However, due to the presence of free cholesterol, the supernatant liquid contains a mixture of HDL and free cholesterol particles. Since the cholesterol in the supernatant is not all HDL, the measured HDL value is erroneous. The amount of HDL reported may be from 15 to 30% higher than the true value. Because this error is not constant, conventional HDL measurement techniques do not provide an accurate guide for comparing the percentage of HDL in the total serum cholesterol of various subjects.

Those who are perceived to have a high risk of heart disease due to high cholesterol levels are often treated with a drug, e.g. lovastatin, to reduce their cholesterol levels. In addition, a low-cholesterol diet is generally suggested. The drug treatment is believed to work by suppressing cholesterol production in the liver. This treatment has several drawbacks: high cost; possible liver damage; and, other side effects. Because of the drawbacks, drug treatment is not recommended for most people in the moderate to high risk categories. Treatment is limited, in many cases, to recommending a low-cholesterol diet. While such a diet may be helpful, it is often not enough, particularly where a patient has difficulty staying on the diet.

SUMMARY OF THE INVENTION

Net HDL cholesterol is measured by separately measuring: the free supernatant cholesterol; and, the combined HDL and free cholesterol in the supernatant. The net HDL value is obtained by subtraction.

The measurement of the combined HDL and free cholesterol fractions is performed in two main steps. First, the LDL and VLDL components are precipitated out of the serum by using an appropriate reagent, e.g. polyethylene glycol (PEG), and centrifuging until the LDL and VLDL are pulled down, leaving a supernatant liquid containing both HDL and free cholesterol. Second, the total cholesterol content of the supernatant is measured by adding a reagent comprising POD, CO, an appropriate enzyme such as a cholesterol esterase or lipase, 4-aminoantipyrine, and a chromogen to a sample of the supernatant liquid; a quinoneimine is produced and its concentration is measured spectroscopically.

To measure the free cholesterol, a sample of the supernatant is treated with a reagent containing peroxidase (POD), cholesterol oxidase (CO), 4-aminoantipyrine, and a chromogen. A quinoneimine is produced chemically in proportion to the amount of free cholesterol originally present in the supernatant; the quantity of quinoneimine produced is measured by uv-visible absorbance spectroscopy.

The net HDL in the specimen may be calculated by subtracting the measured value for free cholesterol from the measured value of the combined HDL and free cholesterol. This net HDL value is a useful indicator for assessing a patient's risk of heart disease.

The level of HDL in the bloodstream may be increased by intake of a diet supplement, mixed to form a non-separating suspension, comprising: polyunsaturated lipids, e.g. safflower oil; phospholipids containing essential fatty acids; anti-oxidants, e.g. Vitamins C or E; and polysaccharides. The supplement is generally given once each morning. The optimum amount of the diet supplement will vary depending upon individual need.

According to the present invention, one object is to provide a method of determining net HDL serum cholesterol.

Another object of the invention is to provide a useful indicator for assessing the risk of heart disease.

A further object of this invention is to provide a method that can effectively raise the level of HDL serum cholesterol.

Other objects and purposes of the present invention will be clear to those skilled in the art from the detailed description of the preferred embodiments and the accompanying examples.

DETAILED DESCRIPTION OF THE PREFERRED EMBODIMENTS

Serum cholesterol comprises several components, as shown by the following expression:

Total cholesterol=HDL+LDL+VLDL+free cholesterol.

Unesterified (free) serum cholesterol may be measured by taking advantage of the following chemical reactions:

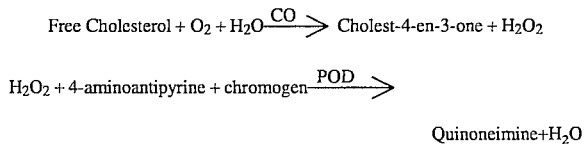

Quinoneimine+H$_2$O

The free cholesterol is oxidized to cholest-4-en-3-one and hydrogen peroxide in a reaction catalyzed by cholesterol oxidase (CO). The peroxide then reacts with 4-aminoantipyrine and the chromogen, in a reaction catalyzed by peroxidase (POD), to form a quinoneimine and water. The amount of quinomeimine produced is directly proportional to the amount of free cholesterol oxidized in the first reaction, and may be measured spectroscopically. Typically, low-sensitivity chromogens such as phenol or p-hydroxybenzoate are used. However, any suitable chromogen may be employed. Preferably, the absorbance at 510 nm is measured and compared to the absorbance of reference standards at that wavelength to determine the quinoneimine concentration.

Total serum cholesterol may be measured in a similar fashion by converting all the esterified cholesterol, found in the HDL, LDL and VLDL particles, to free cholesterol by using the catalyst lipase to break down the cholesterol esters into free cholesterol and fatty acids.

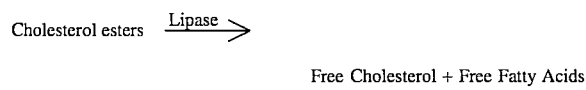

Once these esters are broken down, all the serum cholesterol is in the free form, and thus the total serum cholesterol may be measured by the method described above for measuring free cholesterol.

The HDL cholesterol component may be measured by first separating it from the LDL and VLDL fractions. The serum is treated with Polyethylene glycol (PEG) and then centrifuged, pulling down a precipitate containing the LDL and VLDL. Much of the free serum cholesterol is also pulled down. The supernatant liquid contains the HDL and some free cholesterol. This liquid is then treated with an enzyme such as lipase to break down the HDL and the cholesterol content is measured as described above. This measurement yields the total cholesterol in the supernatant, i.e. HDL and free supernatant cholesterol.

The amount of free cholesterol in the supernatant is measured by treating a sample of supernatant according to the method described above for measuring free serum cholesterol. However, since the amount of free cholesterol in the supernatant is much less than the amount in a serum sample, it has been found that the use of a high-sensitivity chromogen, e.g. 3-hydroxy-2,4,6-triiodobenzoic acid and the like, is preferred for the free supernatant cholesterol measurement.

The net HDL cholesterol in the serum specimen may be calculated by subtracting the measured value of free cholesterol in the supernatant from the measured value of the total cholesterol in the supernatant. The fraction of cholesterol bound in HDL particles may be calculated by dividing the net HDL value by the measured value for the serum total cholesterol. The risk of vascular disease is inversely proportional to the percentage of net HDL. A net HDL level of less than 15% of the total serum cholesterol is associated with high risk whereas levels above 15% are associated with a decreased risk of vascular disease.

The reagents used in the cholesterol measurements described above are preferably buffered. The PEG precipitating reagent is buffered to a pH of approximately 10.0. A free cholesterol reagent containing CO, POD, chromogen and 4-aminoantipyrine is preferably buffered to a pH of about 7.5. Any suitable buffers may be used; standard phosphate buffers and Good buffers have been found to work well.

The HDL particle is composed of approximately 20% cholesterol, 50% protein, and 25% phospholipids. Absorption of sufficient quantities of essential fatty acids (EFA) and long-chain phospholipids is vital to the production of HDL particles. Chylomicrons, very large particles containing essential fatty acids from the diet which are produced in the duodenum and jejunum and quickly cleared once they enter the bloodstream, are required to build lipoprotein moieties and cells. If chylomicrons are not produced in the intestinal mucosa then the system will not produce the types of cell membranes and lipoprotein moleties, e.g. HDL, that protect the organism from atherosclerotic disease. The diet appears to play a major role in determining chylomicron levels. For instance, excessive amounts of dietary saturated fats may play a role in EFA deficiencies.

A pre-emulsified EFA food supplement can increase the quantity of EFA absorbed, and thus raise system-absorbed chylomicron levels. This in turn leads to the production of more HDL particles. Since HDL is believed to scavenge free cholesterol, a decrease in the overall level of cholesterol in the system may also result. The increased level of HDL, and the accompanying decrease in percent LDL and VLDL, may result in less risk of vascular disease.

The dietary supplement of the present invention comprises: polyunsaturated lipids, preferredly lipids having 18 carbon atoms and two or three carbon-carbon double bonds; phospholipids containing essential fatty acids; polysaccharides; and antioxidants, e.g. Vitamin C and/or Vitamin E. This supplement is preferably administered once daily, more preferably in the morning without other foods. The amount of supplement administered will vary based upon individual requirements. One preferred supplement comprises the combination of apple pectin, safflower oil, liquid lecithin, ascorbic acid, and Vitamin E.

The selection of the proper lipids is crucial to the effectiveness of the diet supplement in raising the percentage of HDL cholesterol. The polyunsaturated lipids selected are suitably oils containing predominantly one or more essential fatty acids having a carbon chain length of 18 and two carbon chain double bonds. These oils may optionally contain a significant amount of a fatty acid having an 18-carbon chain containing three double bonds. One preferred oil is safflower oil. Saturated lipids, monounsaturated lipids (i.e. oleic acid), and longer-chain lipids such as are found in marine animals are not believed to be effective for raising HDL levels.

A preferred phospholipid is liquid lecithin. Similar unsaturated phospholipids may be substituted therefor. Saturated (solid) lecithins are not suitable.

Apple pectin is a highly suitable polysaccharide for the practice of this invention. However, similar polysaccharides may be substituted therefor.

Vitamins A and C are suitable antioxidants. However, those skilled in the art will appreciate that other antioxidants may be substituted. The inclusion of one or more vitamins is not essential to the effectiveness of the supplement; thus any compatible antioxidant(s) may be employed in the diet supplement.

The diet supplement comprises an aqueous emulsion containing the ingredients described above. A typical dose of this supplement is about 3–5 ounces for an adult human. However, the amount will vary based upon individual need as determined by cholesterol test results. Dosing is typically done on a daily basis, with the number of days depending on individual need. Often a larger dose, e.g. 5 ounces, is give for about 60 days and a smaller dose, e.g. 3 ounces, is given thereafter.

A three-ounce portion of the diet supplement typically comprises: about from 0.07 to 0.12 g./kg. body weight of polyunsaturated lipids, preferably about 0.08–0.10 g./kg., and most preferably 0.09 g./kg; phospholipids in the amount of approximately 0.025–0.050 g./kg body weight, preferably 0.030–0.045 g./kg. and most preferably 0.039 g./kg.; polysaccharides in the amount of approximately 0.025–0.055 g./kg. body weight, preferably about 0.030–0.045 g./kg, and most preferably 0.039 g./kg.; about 400–800 mg. of antioxidants, preferably about 400–600 mg. Vitamin C and 25– 50 IU vitamin E, most preferably about 500 mg. vitamin C and about 30–40 IU vitamin E; and water. The supplement may optionally be mixed with apple juice, or similar liquids, to make it more palatable.

Emulsification of the supplement ingredients is crucial for proper absorption by the intestines. Therefore, the ingredients must be mixed well when making the diet supplement.

The supplement should be frozen if it is to be stored for an extended period, to prevent undesirable oxidation or other chemical change.

EXAMPLE I

Free serum cholesterol was measured using a working reagent having the following composition:

| | |
|---|---|
| Peroxidase | more than 2000 IU/L |
| Cholesterol Oxidase | more than 100 IU/L |
| 4-Aminoantipyrine | 0.4 mM |
| P-Hydroxybenzoate | 4 mM |
| Sodium Cholate | 3 mM |
| Buffer | pH 7.5 |

A 2.0 ml. aliquot of working reagent was pipetted into each of the clean, dry test tubes to be used for reagent blank, standards, serum control or patients' serum. A 0.02 ml. aliquot of standards, serum control or patients' serum was pipetted into each of the tubes. The contents of each tube was mixed thoroughly and incubated at 37° C. for five minutes. The absorbance at 510nm of the liquids in the serum tubes and in the standard tubes was measured against that of the reagent blank.

EXAMPLE II

The sum of the HDL cholesterol and the free supernatant cholesterol was measured using two working reagents. The first was a PEG reagent comprising 200 g./l. PEG buffered to pH 10.00. The second was a cholesterol reagent comprising:

| | |
|---|---|
| Peroxidase | more than 2000 IU/L |
| Lipase | at least 150,000 IU/L |
| Cholesterol Oxidase | more than 150 IU/L |
| 4-Aminoantipyrine | 0.4 mM |
| Phenol | 4 mM |
| Sodium Cholate | 3 mM |
| Buffer | pH 7.5 |

A 0.2 ml. aliquot of PEG reagent was pipetted into a small tapered centrifuge tube and 0.2 ml. serum was added. The contents were mixed thoroughly and incubated at 25° C. for 10 minutes, then centrifuged at 2000 g for ten minutes at 25° C. The LDL and VLDL was thus precipitated out by the PEG and spun down, leaving a supernatant liquid containing the HDL and free cholesterol, although at one-half the original serum concentration due to the dilution by the reagent.

A 0.02 ml. portion of the supernatant liquid was pipetted into another test tube; 0.02 ml. of each of the standards, and of a serum control, were separately pipetted into other test tubes. Then 0.02 ml. of cholesterol reagent was added to each test tube.

The fluids in the test tubes were thoroughly mixed and then incubated at 37° C. for 10 minutes. Absorbance at 510 nm was measured against a reagent blank for each test solution. The absorbance value of the supernatant test solution was doubled to correct for the dilution effect of the PEG reagent. The concentration of the HDL plus free cholesterol in the supernatant could then be determined by comparing the corrected absorbance to the absorbance of the standard solutions.

EXAMPLE III

The free cholesterol content of the supernatant obtained in Example II was measured by using a cholesterol reagent containing:

| | |
|---|---|
| Peroxidase | More than 2000 IU/L |
| Cholesterol Oxidase | More than 100 IU/L |
| 4-Aminiantipyrine | 0.4 mM |
| 3-Hydroxy-2,4, 6-triiodobenzoic acid | 1.5 mM |
| Sodium Cholate | 3 mM |
| Buffer | pH 7.5 |

A 2.0 ml aliquot of this reagent was pipetted into each test tube; 0.02 ml of supernatant, or of a standard solution, was then pipetted into each test tube. The contents of the tubes were mixed thoroughly and incubated at 25° C. for 5 minutes. The absorbance of each tube was measured against a reagent blank, and the concentration of free cholesterol was calculated as in Example II.

EXAMPLE IV

The total cholesterol in the serum tested in Example II was measured using the same working cholesterol reagent as that used in Example II. A 2.0 ml. aliquot of reagent was pipetted into each test tube; 0.01 ml. of the serum tested in Example II was added to one test tube, and 0.01 ml. of standards and a serum control were individually added to the other tubes. All were mixed well and incubated at 37° C. for 10 minutes. Absorbances were measured, and cholesterol concentration calculated, as in Example II, except that no correction for PEG dilution was needed.

EXAMPLE V

The net HDL concentration of a serum sample was calculated by subtracting the concentration of free supernatant cholesterol, as determined in Example III, from the concentration of HDL and free supernatant cholesterol, as determined in Example II.

[HDL+free]−[free]=[net HDL]

This value was then divided by the measured total serum cholesterol (see Example IV) to calculate the percentage of HDL in the total cholesterol:

$$\frac{[net\ HDL]}{[Total\ Cholesterol]} \times 100\% = \%\ HDL$$

EXAMPLE VI

Ten human subjects were given a 5-ounce dose of an emulsified supplement, on a daily basis, comprising:

| Dietary supplement components | Dosage |
| --- | --- |
| apple pectin | one teaspoon |
| safflower oil | two teaspoons |
| lecithin | one teaspoon |
| ascorbic acid | 500 mg. |
| Vitamin E | 30 IU |

After 60 days they were retested. The changes in serum cholesterol levels are shown in Table I, below.

TABLE I

| Subject # | HDL/mg/dl | | | Free Cholesterol (mg/dl) | | | Total Cholesterol (mg/dl) | | |
| --- | --- | --- | --- | --- | --- | --- | --- | --- | --- |
| | original | final | change | original | final | change | original | final | change |
| 1 | 39 | 58 | +19 | | | | 290 | 278 | −12 |
| 2 | 27 | 70 | +43 | 92 | 89 | −3 | 341 | 315 | −26 |
| 3 | 30 | 45 | +15 | 85 | 70 | −15 | 257 | 250 | −7 |
| 4 | 44 | 60 | +16 | 78 | 62 | −16 | 253 | 268 | +15 |
| 5 | 40 | 50 | +10 | | | | 321 | im | −141 |
| 6 | 40 | 56 | +16 | 86 | 75 | −11 | 299 | 280 | −19 |
| 7 | 27 | 49 | +32 | 41 | 46 | +5 | 172 | 204 | +32 |
| 8 | 36 | 52 | +16 | 60 | 51 | −19 | 207 | 180 | −27 |
| 9 | 43 | 58 | +15 | 60 | 55 | −5 | 185 | 191 | +6 |
| 10 | 47 | 75 | +28 | | | | 264 | 226 | −38 |
| Average | | | +21 | | | −9 | | | −22 |

I claim:

1. A method for ascertaining the level of risk for a human patient to the advent of vascular disease; comprising the steps of:

a) determining on a percentage basis the net HDL cholesterol level of said human patient's blood serum, wherein said determination is accomplished as follows:

i) taking a sample of blood serum and precipitating LDL and VLDL fractions, ii) separating and isolating the precipitant from a supernatant, iii) treating said supernatant with cholesterol esterase or lipase in an amount to substantially de-esterify HDL cholesterol in said supernatant, iv) converting substantially all of said cholesterol in said supernatant to $H_2O_2$ and cholest-4-en-3-one, v) converting all $H_2O_2$ to quinoneimine in said supernatant, vi) determining the amount of quinoneimine in said supernatant, vii) converting said amount into a concentration of HDL cholesterol and free cholesterol, viii) performing steps (iv) to (vi) on a second sample of said supernatant from step (ii) and converting said amount into a concentration of free cholesterol, ix) determining net HDL cholesterol by subtracting the concentration of free cholesterol from step (viii) from the concentration of HDL cholesterol and free cholesterol from step (vii); and b) assigning an increased risk of vascular disease for patients exhibiting concentrations of net HDL cholesterol that are less than 15% of total serum cholesterol.

2. The method of claim 1 wherein said separation of precipitate is accomplished via centrifugation.

3. The method of claim 2 wherein said concentration of quinoneimine is determined spectroscopically.

* * * * *